United States Patent
Haavig et al.

(10) Patent No.: US 6,421,121 B1
(45) Date of Patent: Jul. 16, 2002

(54) METHOD AND APPARATUS FOR RAPID PARTICLE IDENTIFICATION UTILIZING SCATTERED LIGHT HISTOGRAMS

(75) Inventors: David L. Haavig, Oceanside; Gary Lorden, Pasadena, both of CA (US)

(73) Assignee: Micro Imaging Technology, Laguna Hills, CA (US)

(*) Notice: Subject to any disclaimer, the term of this patent is extended or adjusted under 35 U.S.C. 154(b) by 0 days.

(21) Appl. No.: 09/501,840

(22) Filed: Feb. 10, 2000

(51) Int. Cl.[7] .................................................. G01N 21/00
(52) U.S. Cl. ......................................... 356/338; 356/343
(58) Field of Search ................................. 356/335, 336, 356/337, 338, 343

(56) References Cited

U.S. PATENT DOCUMENTS

| | | | | |
|---|---|---|---|---|
| 4,735,504 A | * | 4/1988 | Tycko | .......................... 356/336 |
| 4,781,460 A | * | 11/1988 | Bott | ............................. 356/336 |
| 5,367,474 A | * | 11/1994 | Auer et al. | .................. 364/555 |
| 5,760,900 A | * | 6/1998 | Ito et al. | ...................... 356/338 |

* cited by examiner

Primary Examiner—Frank G. Font
Assistant Examiner—Michael P. Stafira
(74) Attorney, Agent, or Firm—Frank Frisenda, Jr.

(57) ABSTRACT

Unique methods and apparatus are provided for rapidly identifying microscopic particles, such as protozoa and other microbes suspended in a fluid or gas. In one embodied form, the method comprises illuminating the particles to be detected with an intense light source such as a laser, detecting scattered light by means of an array of optical sensors surrounding a detection zone, converting the detected light to an electrical signal, and comparing the derived signal with at least one frequency-of-occurrence/probability histogram curve to qualitatively and/or quantitatively identify the microscopic particles present.

27 Claims, 4 Drawing Sheets

METHOD AND APPARATUS FOR RAPID PARTICLE IDENTIFICATION UTILIZING SCATTERED LIGHT HISTOGRAMS

BACKGROUND OF THE INVENTION

The present invention provides unique methods and apparatus for identifying microscopic particles, such as protozoa and other microbes suspended in a fluid or gas.

Currently accepted methods for identification of pathogenic microscopic particles require relatively long, labor-intensive process. For instance, to determine whether Cryptosporidium parvum or Giardia lamblia is present in drinking water, suppliers must employ the USEPA method 1622, a long and labor-intensive procedure. Clinical laboratories and food inspectors also must use long labor-intensive procedures to locate and identify harmful bacteria.

Unfortunately, there are many circumstances when positive identification of a microbe cannot wait. A contamination of drinking water by Cryptosporidium must be recognized immediately, before the water is delivered to homes. Likewise, identification of a specific cause of a disease, such as bacterial meningitis, many times cannot wait the hours required. Finally, detection and identification of bacteria in food sources, such as beef, takes so long that in most cases, the food is distributed before the problem is discovered.

A variety of methods and apparatus exist for detection of microscopic organisms. For instance, De Leon, et al. in U.S. Pat. No. 5,770,368 teaches Cryptosporidium detection methods. The viability or infectivity of the encysted forms can be determined by synthesizing a cDNA from an induced HSP RNA template using a primer that is specific for particular genus or species of protozoa, followed by enzymatic amplification of cDNA. Alternatively, infectivity can be determined by amplifying HSP DNA from infected cells using a primer pair that is specific for a particular genus or species of protozoa.

Steele, et al. in U.S. Pat. No. 5,693,472 discloses detection of Cryptosporidium parvum. A method and kit for the detection of Cryptosporidium parvum in aquatic and biological samples such as surface water or feces is described. The method relies on the use of primers to detect all or a portion of at least one DNA sequence characteristic of Cryptosporidium parvum, the sequence being all or part of the genomic regions referred to as 38G and HemA contained within recombinant plasmids pINV38G, and pHem4, respectively.

Pleass, et al. in U.S. Pat. No. 5,229,849 discloses laser Doppler spectrometer for the statistical study of the behavior of microscopic organisms. An improved method and system of monitoring and identifying microbiota swimming in a fluid or moving across surfaces in a fluid provides a sensitive method for rapidly measuring very small changes in activity, and detecting and identifying individual microbes in relatively large volumes of fluid, even in the presence of detritus. The system comprises a laser station, a sample collector station, a picture taking station and a monitoring station.

Wyatt, et al. in U.S. Pat. No. 4,548,500 teaches process and apparatus for identifying or characterizing small particles. An apparatus and process are described for the characterization and/or identification of individual microparticles based upon the measurement of certain optical observables produced as each particle passes through a beam of light, or other electromagnetic radiation. A fine beam of, preferably, monochromatic, linearly polarized light passes through a spherical array of detectors, or fiber optics means, to transmit incident light to a set of detector means, and a stream of particles intersects the beam at the center of the spherical array. Selected observables calculated from the detected scattered radiation are then used to recall specific maps, from a computer memory means, one for each observable.

Lee, et al. in U.S. Pat. No. 5,473,428 disclose an interferometric temperature sensing system having a coupled laser diode wherein the magnitude is adjusted corresponding to a prior feedback laser beam. An interferometric temperature sensing system provides a simplified design for accurately processing an interference fringe pattern using self coupling effects of a laser detection element, where a laser diode and an optical detection element are combined in one package.

Curtis Thompson's U.S. Pat. No. 5,582,985 teaches detection of mycobacteria. The invention provides a method, compositions, and kits useful for detecting mycobacteria in a sample. The method includes contacting the sample with a formaldehyde solution, an organic solvent, and a protein-degrading agent prior to hybridizing a mycobacteria-specific nucleic acid probe to the sample. The invention has particular utility in detection and susceptibility screening of human-disease causing mycobacteria such as mycobacterium tuberculosis.

SUMMARY OF THE INVENTION

The unique system of the present invention provides accurate and valid measurements for identifying a wide variety of microscopic particles, such as protozoa and other microbes suspended in a fluid or gas. The inventive methodology provides a procedure for the quantitative and qualitative identification of particle species derived from measurement of light scattered by the particle that is collected by an array of optical sensors surrounding the suspended particle, in a convenient and reliable manner.

In more detail, the light scattered by the suspended particle is detected by the sensor array and converted to an electrical signal, e.g. a voltage. The voltage from each sensor is entered into a modifying means component where the voltages are digitized and the resulting values are used as fingerprints for particle identification. The unique modifying component comprises prediction formulas derived from one or more sets of empirically determined one-dimensional or multi-dimensional probability histograms that are functions of one or more mathematical combinations of the digitized voltages. Each set consists of individual probability histograms, which give the likelihood that observed values of specific combinations of digitized voltages were produced by a specific particle species. Thus, the unique modifying component of the inventive system interprets the measured signals as "species specific" when the prediction formulas result in probability values that are large for a specific species.

In one embodied form, the inventive method for rapidly detecting and identifying microscopic particles for quantitative and qualitative measurement comprises the steps of:

a) suspending the particle to be identified in a control fluid contained within a sample chamber;

b) holding the sample chamber in a prescribed orientation with respect to an intense light source;

c) illuminating the sample chamber with said light source;

d) collecting and measuring the scattered light from the sample chamber by means of an array of optical sensors surrounding the sample chamber;

e) converting a voltage output from the array of sensors to a digital signal as the particle passes through the intense light source; and f) comparing the derived signal with a library of probability histograms and statistically classifying the resultant data to identify the microscopic particles present.

In accordance with the present invention, the library consists of histograms for each particle species encompassed by a statistical classification algorithm that calculates the probabilities that the associated signal was produced by those particle species. The probability histogram is derived empirically from a measure of the frequency that a species of microparticle is associated with a specific range of values of a mathematical combination of the digitized sensor voltages. Thus, the frequency-of-occurrence histogram can be produced for one mathematical combination, i.e., a one-dimensional analysis or alternatively, can be produced for multiple mathematical combinations simultaneously, i.e., a multi-dimensional analysis.

In a presently preferred embodied form, the inventive apparatus comprises, in combination:

a) a polarized laser that produces a beam waist;

b) an optical chassis including multiple light detectors, each light detector positioned around and oriented to view, without obscuration, a common region of regard of the laser beam waist;

c) a sample chamber for containing a fluid sample to be analyzed;

d) means for holding the sample chamber in a prescribed orientation with respect to the laser beam waist and in the common region of regard of the light detectors;

e) means for causing the particles in the sample to circulate through the laser beam waist;

f) means for covering the light source and optical chassis to create a dark enclosure;

g) means for converting the light intensity values measured by the detectors into digital values:

h) means for continuously entering the digital values into a computer;

i) means for determining when a particle has entered the light beam at the common region of regard based on the digitized measurements;

j) means for converting the digitized values to calibrated values;

k) means for extracting Event Descriptors from the digitized and calibrated event data;

l) means for calculating Discriminant Function values from the Event Descriptors;

m) means for defining probability histograms that enable the calculation of the probability that a Discriminant Function value calculated from measured values was caused by a specific particle species;

n) means for identifying the most effective Discriminant Functions.

o) means for storing the probability histograms and Discriminant Functions in an Identification Library, one histogram for each particle species that can be identified and each Discriminant Function;

p) means for retrieving previously stored probability histograms and Discriminant Functions, one probability histogram for each particle species that can be identified with the Identification Library and each Discriminant Function;

q) means for calculating the probability for each particle species in the library for a given value of a Discriminant Function;

r) means for combining probabilities for each particle species that can be identified with the Identification Library; and s) means for identifying the unknown particle based on a threshold.

DETAILED DESCRIPTION OF THE PREFERRED EMBODIMENTS

Figure 1:
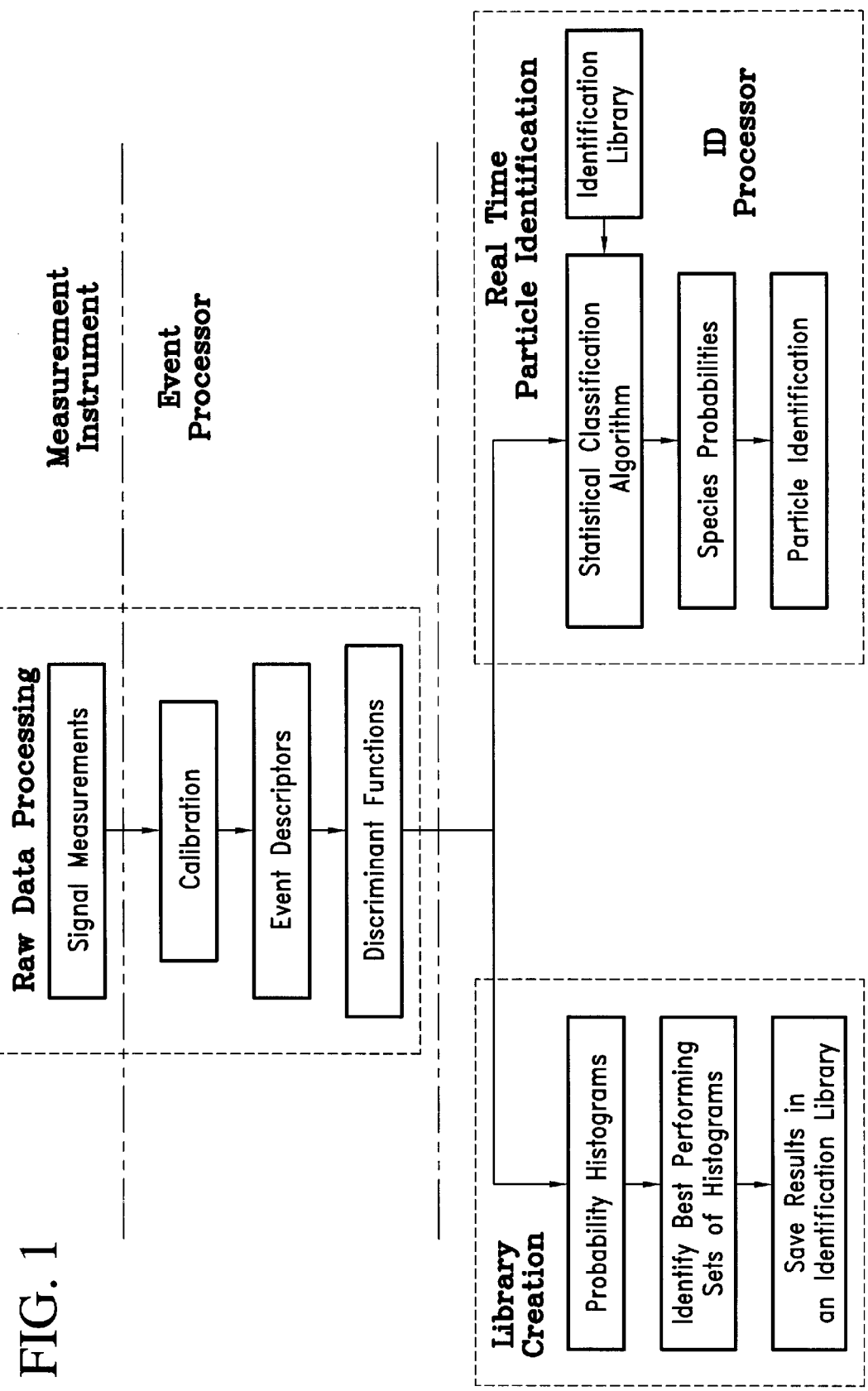
FIG. 1 is a flow chart showing the steps to create an Identification Library and to identify particles using the Identification Library using the preferred embodied form of this invention.

The present invention provides a unique method and apparatus for a microscopic particle identification method based on a statistical analysis of measured data. The method depends on three interrelated parts (see FIG. 1): The measurement instrument and raw data processing system; the creation of an Identification Library; and the use of the Identification Library.

This invention provides the means to rapidly detect and identify microbes and other types of particles. The system is based on a measure and analysis of light scattered off particles as they pass through an intense collimated light source. When particles are comparable to and somewhat larger than the wavelength of the incident light, light predominantly diffracts off the particle, scattering light energy in all directions. The light intensity in the various directions depends explicitly on the size and shape of the particle and wavelength of the incident light. In principle, one may calculate a particle size and shape from a high angular resolution measure of the light intensity and electromagnetic phase of all the scattered radiation. This, in fact, is a common practice in aerospace when dealing with radar signatures of vehicles. However, this technique is impractical when dealing with visible light. Additionally, measuring the exact size and shape of particles, such as bacteria, is not useful for identification due to natural size and shape variations. In accordance with the present invention, a system for particle identification by measuring only a small part of the scattered light is provided. By comparing the measured result with a library of previously made measurements, performed on a variety of types of particles, accurate particle identification is achieved.

The following definitions will be helpful to create a more complete description of the preferred embodiments.

The term "fluid" shall mean a liquid or gas media.

The term "light" shall mean electromagnetic radiation.

The term "common region of regard" shall mean a small region in space that is viewed simultaneously by all light detectors.

The term "without obscuration" shall mean no visual blocking, warping or vignetting.

The term "transparent" shall mean optically clear at the wavelength of employed light.

The term "sample chamber" shall mean a transparent enclosure that contains the sample.

The term "detectors" shall mean an electronic device that is sensitive to light and converts the incident light into a voltage or current with magnitude proportional to the incident light intensity.

The term "optical chassis" shall mean the framework, optical detectors and electronics that surround the sample chamber.

The term "apply calibration" shall mean to make corrections to the raw measured data such that measurements of standards will result in correct values.

The term "particle species" shall mean an individual class of particle such as a species of a microorganism or pollen or the type of article such as red blood cell, etc.

The term "event" shall mean a set of measured scattered light data taken as one particle passes through the light beam.

The term "frequency-of-occurrence histogram" shall mean a measure of how often the measurement of a particle species results in a specific value range for a given calculation of a mathematical combination of specific measurements.

The term "probability histogram" shall mean a normalized frequency-of-occurrence histogram such that the area under the curve (one-dimensional case) or the volume under the curve (multi-dimensional case) is one.

Figure 2:
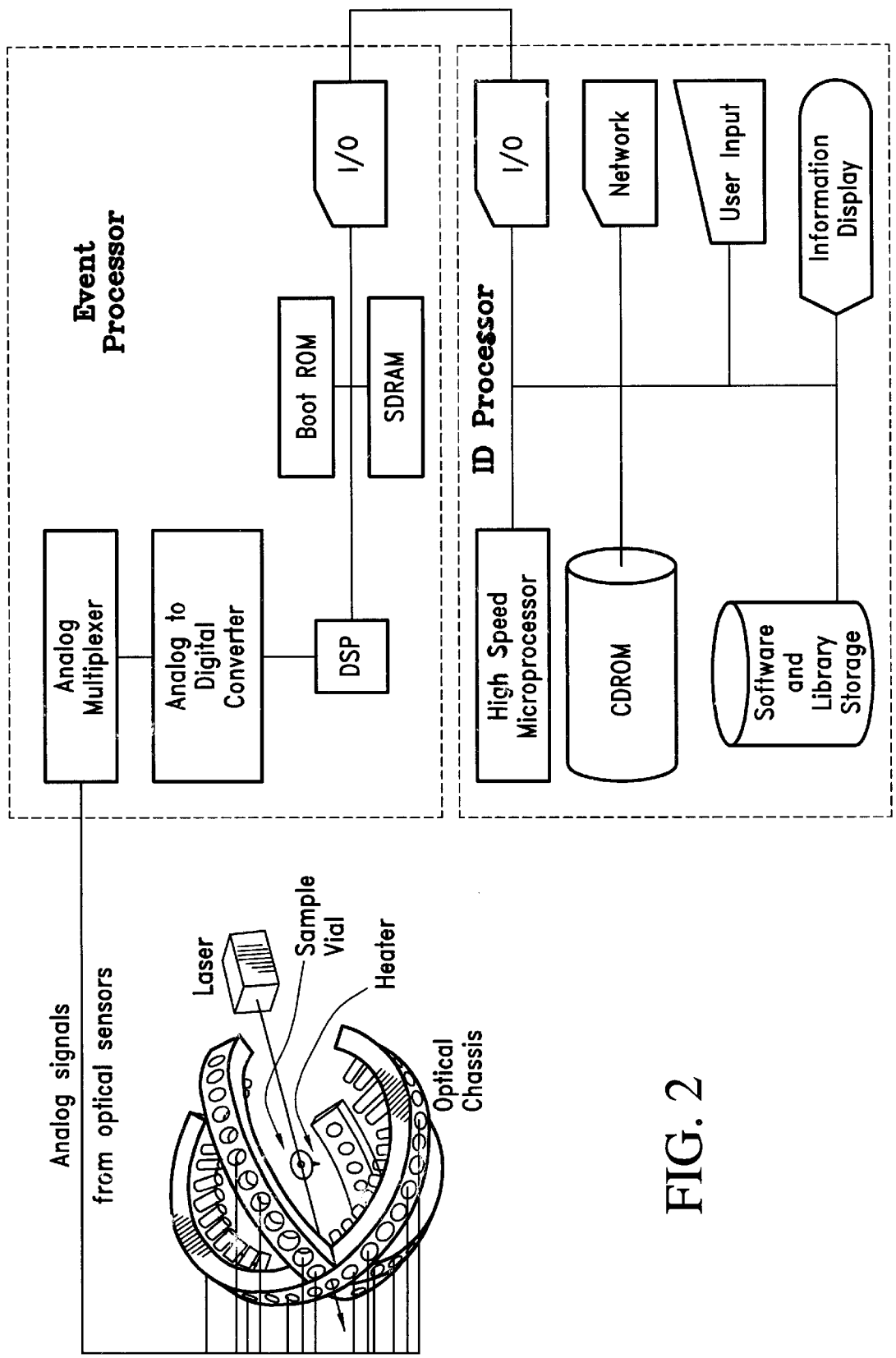
FIG. 2 is a schematic of the complete identification system.

In one embodied form, the inventive method for rapidly detecting and identifying microscopic particles for quantitative and qualitative measurement (the third of three interrelated parts) uses the measurement instrument shown in FIG. 2 and comprises the steps of:

a) suspending the particle to be identified in a ultra-high quality water contained within a glass vial;

b) holding the sample vial in an intense laser source such that the beam waist passes through the center;

c) collecting and measuring the scattered light from the glass vial by means of an array of optical sensors surrounding the sample chamber;

d) converting a voltage output from the array of sensors to a digital signal as the particle passes through the intense light source; and e) comparing the derived signal to at least one set of probability histograms to identify the microscopic particles present.

Accordingly, the identification of a particle species proceeds by initially measuring a statistically significant number of that species and deducing pertinent information from the measurements. After the collecting and archiving the relevant information in an Identification Library, identification of unknown particles proceeds by comparison of new measurements with the archived library of particle characteristics.

The system utilizes light scattered off particles that pass through the intense light source. FIG. 2 shows a schematic of one embodied form of an instrument to measure the scattered light and perform library creation and particle identification. An Optical Chassis provides the framework to support the optical detectors and constrain their field-of-view to a single common region of regard. The optical detectors collect and measure the intensity of the light scattered outside a sample chamber. An Event Processor subsystem continuously digitizes the voltage generated by the detectors and monitors the digitized voltage to dynamically extract a background signal and to determine when a particle passes through the laser beam.

When the Event Processor detects a particle passing through the laser beam, the processor keeps the digitized voltage from each detector until the particle passes completely through the beam. After the particle passes through the beam, the Event Processor applies calibration, then extracts from the digitized data, specific data (Event Descriptors) required by the particle identification algorithm and passes the Descriptors to the ID processor subsystem.

The ID Processor subsystem uses the Event Descriptors to form Discriminant Function values to cross-reference into the particle species Identification Library. The library contains numerous sets of probability histograms that can be used to calculate the probability that observed Discriminant Function values resulted from specific particle species. The ID Processor uses the probability histograms and a statistical classification algorithm to deduce the identity of the particle that passed through the laser beam. The ID Processor presents the identity of the particle on the display.

Thus, the first inventive process stage creates the Identification Library utilizing a large number of measurements by the measurement instrument. The second inventive process stage uses the measurement instrument and library to identify unknown particles.

Figure 3:
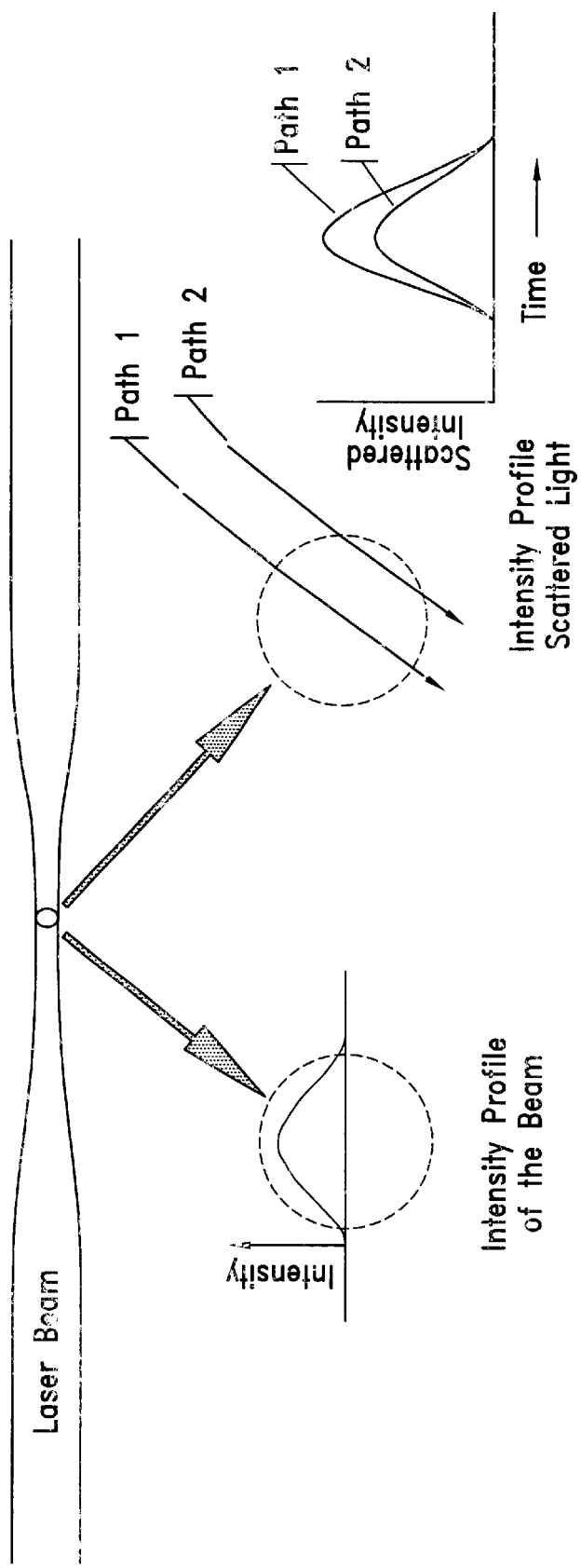
FIG. 3 is a close up of the beam waist of the laser. If the laser has a Gaussian intensity profile, spherical particles passing through the laser beam will scatter light that has a Gaussian shape versus time.

Understanding the Library creation process relies on understanding data measured for a spherical particle. When a spherical particle passes through the collimated beam, the photodetectors measure a time dependent intensity dependent on both the particle speed and the cross-sectional intensity profile of the laser. FIG. 3 shows that when the laser has a Gaussian cross-sectional intensity profile, a spherical particle will also have a Gaussian scattered light intensity versus time (note: the particle is much smaller than the diameter of the beam). Thus, v(d,t), the voltage measured on detector, d, as a function of time, t, is also Gaussian. The same particle passing through the beam waist along different paths will show Gaussian profiles with different magnitudes. Dividing the measured values, at each instant in time, by a sum of one or more of the detector values at the same instant in time removes this path dependency. Thus:

$$v'(d,t) = v(d,t)/\Sigma_{d'} v(d',t). \quad \text{Equation (1)}$$

Here, d' is some or all of the detectors. When the particles are spherical, the normalized values, v'(d,t), are constant as long as the signal strength is large enough. Additionally, the value is independent of the path taken by the particle as it passes through the laser beam.

The value of the ratio for spherical particles from equation (1) is predictable when the wavelength, particle diameter and the index-of-refraction of the particle and the fluid are known. Thus, for spherical particles, it is sufficient to use a single ratioed value from each detector to characterize the particle that passed through the beam. These single ratioed values from each detector are called Event Descriptors since they uniquely describe the source of the event, that is, the particle that caused the event. In the following, ED(d) shall represent the Event Descriptor for detector d, that is, ED(d) = $v'(d,t_I)$ where $t_I$ is a specific instant in time. Every spherical particle with the same size will produce the same Event Descriptors, ED(d). Thus, given a measurement of a spherical particle event, the diameter of the particle can be derived, in principle, from the values of the event descriptors.

When the particle is not a sphere, the Event Descriptors of equation (1) are no longer constant. A plot of v'(d,t) versus time will not result in straight lines. The shape of the curve depends on the orientation of the particle as it passes through the beam. The same particle passing through the laser beam repeatedly will produce a variety of plot shapes. Likewise, different particles of the same particle species will also produce a variety of plot shapes. As a result, the Event Descriptors as described above depend on time. Consequently, to account for non-spherical particles, the concept of the Event Descriptor is relaxed to denote data that simply is characteristic of the event even though the descriptor value may not be constant in time for the particle species.

The identification method requires a specific scheme to extract Event Descriptors from the event data. There are a variety of schemes. Two are:

1. Select an Event Descriptor value that is the maximum value of ED(d,t)=v'(d,t) attained during the event. That is: $ED_d = \max(v(d,t)/\Sigma_{d'} v(d',t))$.
2. Select an Event Descriptor value that is the value of $ED(d,t_n) = v'(d,t_n)$ at the time, $t_n$, when the value $v'(d_n,t)$ is a maximum for a specific detector, $d_n$, during the event. That is: $ED_d = v(d,t'_n)/\Sigma_{d'} v(d',t'_n)$ where $t'_n$ is the time when detector d=n is a maximum.

Since the event data measured when a non-spherical particle passes through the laser beam depends on its orientation, one cannot directly identify the particle given the Event Descriptor values. However, one can use a statistical analysis to predict what the particle was. Measuring many particles of the same species will produce a family of Event Descriptor values. The family of values describes the range of values that the Event Descriptors take. It is important to note that the range of values is limited in extent. Plotting these measured values as a frequency-of-occurrence histogram versus Event Descriptor value results in a graph similar to that in FIG. 4. As this graph indicates, the range of values for Event Descriptors are limited and, more importantly, some values are more likely than others are.

Figure 4:
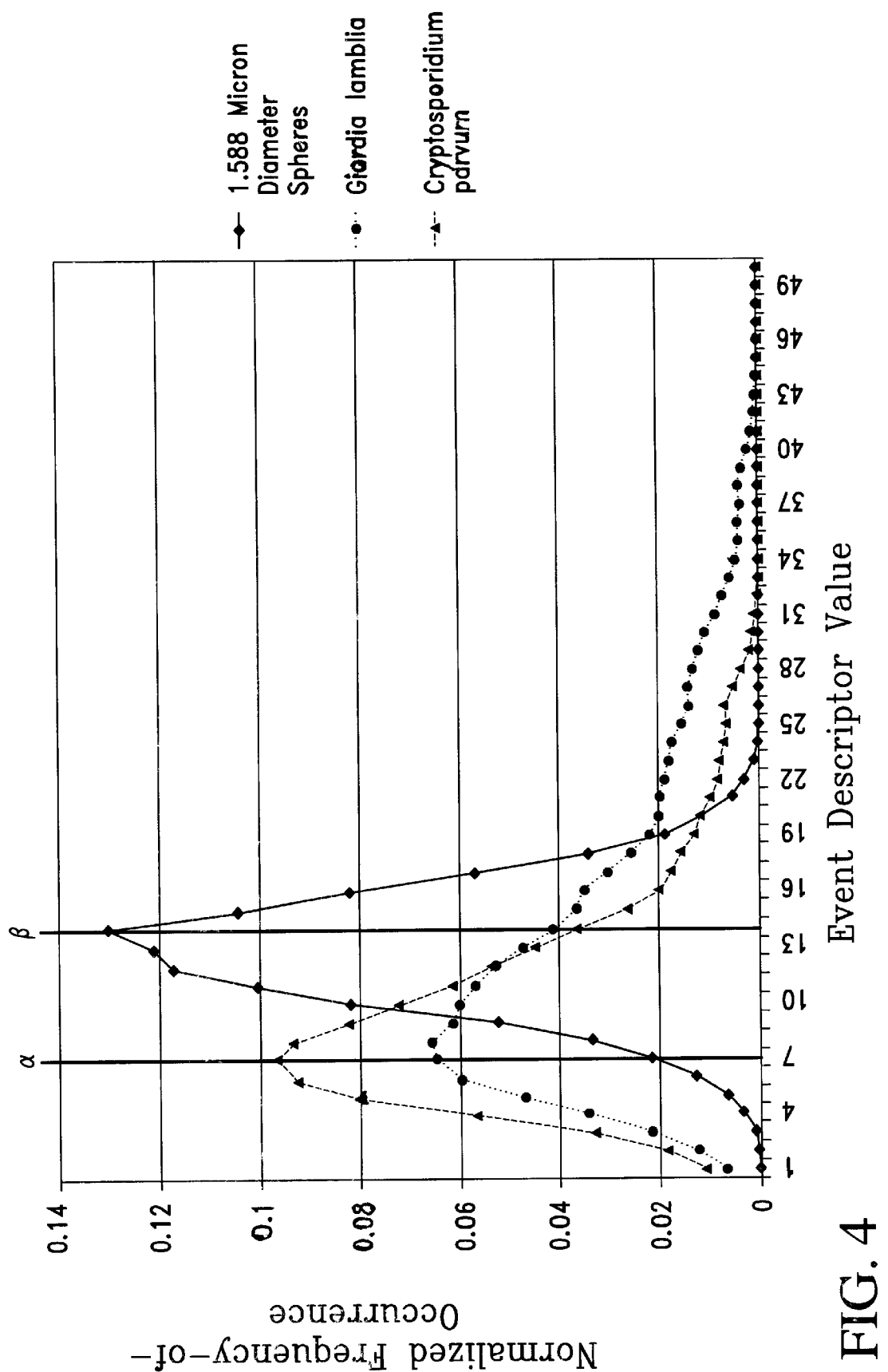
FIG. 4 shows three normalized frequency-of-occurrence histograms. These plots show results for measured data of three particle species: a sample of 1.588±0.025-micrometer diameter polystyrene spheres (standard deviation of 0.016 micrometer), Giardia lamblia and Cryptosporidium parvum.

A frequency-of-occurrence histogram plot for a different particle species will result in a somewhat different histogram graph since the particles will have different size, shape or optical characteristics. FIG. 4 shows normalized histogram plots for three different particle species: Giardia lamblia, Cryptosporidium parvum and a sample of 1.588 micrometer diameter polystyrene spheres for an Event Descriptor, $ED_1$. Given a specific measured value for $ED_1$, such as the point α on the graph, one can deduce that the particle is likely to be a Giardia lamblia or Cryptosporidium. Likewise, if the value is β, then the particle is likely to be a 1.588-micrometer diameter sphere. However, the identification is not absolute. At both point's α and β, there is still a non-zero chance that the event was caused by any one of three particle species.

Clearly, the process requires additional information to increase the likelihood of an accurate identification. The additional information comes from using another set of histograms for a different Event Descriptor, $ED_2$ and so on. The identification process becomes a matter of deducing a particle species from the probability that measured Event Descriptor values were produced by the different particles in the data set of pre-measured histogram curves. The data set of pre-measured normalized histograms is called an Identification Library.

The Library Creation stage starts with the Event Descriptors extracted from the event data and processed by the measurement instrument. The Event Descriptors are reorganized into a large set of Discriminant Functions. Probability histograms for each function and each different particle species to be included in the library are calculated. The strength of each Discriminant Function in providing species-to-species distinction is calculated. The best Discriminant Functions are identified and pertinent data saved for use by the identification procedure.

Discriminant Functions enhance the distinction between particle species. Consider data for two different spherical diameters. One finds cases where the value $ED_1$ is large for one sphere and small for the other sphere while $ED_2$ is small for the first sphere and large for the second. In this case, the ratio $ED_1/ED_2$ is a good discriminator between the two different spheres. This ratio is large for one sphere diameter and small for the other. In this case, a histogram for the values resulting from the Discriminant Function $DF=ED_1/ED_2$ will show greater separation between the curves for the two different particle species than the histograms of the individual Event Descriptors.

Discriminant Functions are simply generalizations of the Event Descriptor concept. For example, the following three relations between Event Descriptors are each Discriminant Functions: $DF_1 = ED_1$, $DF_2 = 1/ED_2$ and $DF_3 = ED_1/ED_2$. Since the Discriminant Functions include the individual Event Descriptors, the following discussion will only use Discriminant Function.

The histograms are easier to use when normalized. That is, the area under the curve is one (one-dimensional case) or the volume under the curve is one (multi-dimensional case). The resulting curves then are like probability densities. These probability histograms now give directly the probability that a specific Discriminant Function value resulted from a measurement of a specific particle species.

As described above, one probability histogram for each particle species cannot classify a measured Event as a specific particle species. Consequently, a set of densities derived from a set of Discriminant Functions is required. Unfortunately, there may exist Discriminant Functions that do not exhibit good separation between the probability histogram curves for different particle species as demonstrated in FIG. 4. While the separation between Giardia and the spheres and between Cryptosporidium and the spheres is good, the separation between Giardia and Cryptosporidium is not very good. Consequently, the Discriminant Function plotted in FIG. 4 does not provide useful identification information distinction between Giardia and Cryptosporidium. The choice of which set of Discriminant Functions to use for identification is crucial: Discriminant Functions cannot be chosen haphazardly. as Additionally, there is no a priori reason to select one set of Discriminant Functions over another. Fortunately, given the high speed and large data handling capabilities of modern computers, one can simply calculate the densities for a large set of functions, sort through the results and identify those that provide good separation between the probability histogram curves for individual particle species.

With the best performing set of Discriminant Functions identified, the Identification Library may be created and archived. The Library must contain a list of the species encompassed by the probability histograms. Each set of probability histograms must have its associated Discriminant Function.

To identify unknown particles with the Identification Library, load the library into the identification computer memory. The measurement instrument and raw data analysis procedure measures the unknown particle and extracts Event Descriptor data as described.

The identification procedure begins by measuring and collecting the data for an unknown particle as it passes through the laser beam. The Event Processor digitizes the resulting signals and extracts the Event Descriptor data from the event. The Event Processor then passes the Event Descriptor data to the ID Processor that attempts to identify the particle.

The ID Processor begins by calculating values for the Discriminant Functions from the Event Descriptors for the first set of probability histograms in the library. Looking up or interpolating the probability values from the probability histogram for each respective particle species and applying a statistical classification algorithm determines the probability that a specific particle species generated these Discriminant Function values. The result is an array of probabilities associated with these first Discriminant Functions: p(df, species), where df in this case is the Discriminant Function set number, 1 in this case—that is, it is the first set of Discriminant Functions. The ID Processor repeats this process for all sets of Discriminant Functions and their associated probability histograms in the library.

One possible statistical classification algorithm uses the set of probability values described as p(df, species), where df is the specific Discriminant Function and species is the particle species, in the following way. The probabilities for each different particle species (species) are combined to form a single probability value for that species:

$$p(\text{species}) = \Sigma_{df} W(df) \times p(df, \text{species}),$$

where W(df) is a weighting for the probability histogram resulting from the Discriminant Function set, df.

Particle species identification occurs by proper interpretation of these final probability values. One embodied interpretation is to use thresholds. If p(species)>t(species), where t(species) is the threshold value for a specific particle species, and all other values are less than their thresholds, then the particle is identified as that species. If more than one probability is above its respective threshold or if no probabilities are above threshold then the particle cannot be identified.

In a presently preferred embodied form, the inventive apparatus comprises, in combination:

a) a polarized laser that produces a beam waist;
b) an optical chassis including multiple light detectors, each light detector positioned around and oriented to view, without obscuration, a common region of regard of the laser beam waist;
c) a sample chamber for containing a fluid sample to be analyzed;
d) means for holding the sample chamber in a prescribed orientation with respect to the laser beam waist and in the common region of regard of the light detectors;
e) means for causing the particles in the sample to circulate through the laser beam waist;
f) means for covering the light source and optical chassis to create a dark enclosure;
g) means for converting the light intensity values measured by the detectors into digital values;
h) means for continuously entering the digital values into a computer;
i) means for determining when a particle has entered the light beam at the common region of regard based on the digitized measurements;
j) means for converting the digitized values to calibrated values;
k) means for extracting Event Descriptors from the digitized and calibrated event data;
l) means for calculating Discriminant Function values from the Event Descriptors;
m) means for defining probability histograms that enable the calculation of the probability that a Discriminant Function value calculated from measured values was caused by a specific particle species;
n) means for identifying the most effective Discriminant Functions.
o) means for storing the probability histograms and Discriminant Functions in an Identification Library, one histogram for each particle species that can be identified and each Discriminant Function;
p) means for retrieving previously stored probability histograms and Discriminant Functions, one probability histogram for each particle species that can be identified with the Identification Library and each Discriminant Function;
q) means for calculating the probability for each particle species in the library for a given value of a Discriminant Function;
r) means for combining probabilities for each particle species that can be identified with the Identification Library; and
s) means for identifying the unknown particle based on a threshold.

What is claimed is:

1. A method for rapidly detecting and identifying microscopic particles for quantitative and qualitative measurement comprising the steps of:

a) suspending the particles to be identified in a control fluid contained within a sample chamber;
b) holding the sample chamber in a prescribed orientation with respect to an intense light source;
c) illuminating the sample chamber with said intense light source;
d) collecting and measuring the scattered light from the sample chamber by means of an array of optical sensors surrounding the sample chamber;
e) converting a voltage output from the array of sensors to a digitized detector value at each instant in time and normalized by the sum of one or more digitized detector values to produce event descriptors; and
f) comparing the derived signal with a set of frequency-of-occurrence/probability histograms to enable the identification of the microscopic particles present by means of a statistical classification algorithm.

2. The method of claim 1 wherein the event descriptors are the maximum value measured by each sensor during the event.

3. The method of claim 1 wherein the event descriptors are equal to the digitized detector values at one instant in time.

4. The method of claim 1 wherein said sample chamber comprises a particle circulation means.

5. The method of claim 1 wherein the particle to be identified is immersed in a gas.

6. The method of claim 1 wherein the particle to be identified is immersed in a fluid.

7. The method of claim 1 wherein the intense light source is produced by multiple co-aligned lasers each emitting at different wavelengths.

8. The method of claim 1 wherein the intense light source is produced by a single multi-wavelength laser.

9. The method of claim 1 wherein the optical sensors are solid-state photovoltaic devices.

10. The method of claim 1 wherein the optical sensors are solid-state photocurrent devices.

11. The method of claim 1, wherein the optical sensors are solid-state avalanche devices.

12. The method of claim 1 wherein the optical sensors are photomultiplier devices.

13. The method of claim 1 wherein the optical sensors incorporate polarization analyzers to make them sense only one polarization direction.

14. The method of claim 1 wherein the optical sensors employ fiber optic cables to gather incident light and transport the light to the detectors.

15. The method of claim 8 wherein the fiber optic cables incorporate polarization analyzers to make them sense only one polarization direction.

16. The method of claim 1 wherein the sample chamber is a glass vial.

17. The method of claim 1 wherein the sample chamber is a plastic vial.

18. The method of claim 1 wherein the sample chamber allows for continuous flowing of the fluid.

19. The method of claim 1 wherein the probability histograms are a function of n Discriminant Function resulting in one n-dimensional histogram for each particle species where n is an integer.

20. The method of claim 19 wherein the complete set of n-dimensional histograms and the n Discriminant Functions for each function is saved in an Identification Library means.

21. The method of claim 20 wherein the complete set of n-dimensional probability histograms and the n Discriminant Functions for each histogram in the identification Library is retrieved from memory means previously.

22. The method of claim 19 wherein the outputs of a statistical classification algorithm based upon probability histograms for each particle species are reduced to a single value of 1 if above threshold and value of 0 if below the threshold.

23. The method of claim 1 wherein the particle circulation means is a heater applied to the outside of the chamber.

24. The method of claim 23 wherein the heater is applied to the bottom of the sample chamber.

25. The method of claim 1 wherein the particle circulation means is a cooler applied to the outside of the chamber.

26. The method of claim 25 wherein the cooler is a thermoelectric device.

27. An method for rapidly detecting and identifying microscopic particles for quantitative and qualitative measurement comprising the steps of:
 a) a polarized laser that produces a beam waist;
 b) an optical chassis including multiple light detectors, each light detector positioned around and oriented to view, without obscuration, a common region of regard of the laser beam waist;
 c) a sample chamber for containing a fluid sample to be analyzed;
 d) means for holding the sample chamber in a prescribed orientation with respect to the laser beam waist and in the common region of regard of the light detectors;
 e) means for causing the particles in the sample to circulate through the laser beam waist;
 f) means for covering the light source and optical chassis to create a dark enclosure;
 g) means for converting the light intensity values measured by the detectors into digital values;
 h) means for continuously entering the digital values into a computer;
 i) means for determining when a particle has entered the light beam at the common region of regard based on the digitized measurements;
 j) means for converting the digitized values to calibrated values;
 k) means for extracting Event Descriptors from the digitized and calibrated event data;
 l) means for calculating Discriminant Function values from the Event Descriptors;
 m) means for defining probability histograms that enable the calculation of the probability that a Discriminant Function value calculated from measured values was caused by a specific particle species;
 n) means for identifying the most effective Discriminant Functions
 o) means for storing the probability histograms and Discriminant Functions in an Identification Library, one histogram for each particle species that can be identified and each Discriminant Function;
 p) means for retrieving previously stored probability histograms and Discriminant Functions, one probability histogram for each particle species that can be identified with the Identification Library and each Discriminant Function;
 q) means for calculating the probability for each particle species in the library for a given value of a Discriminant Function;
 r) means for combining probabilities for each particle species that can be identified with the Identification Library; and
 s) means for identifying the unknown particle based on a threshold.

* * * * *